United States Patent [19]

Shutske

[11] Patent Number: 4,868,188
[45] Date of Patent: Sep. 19, 1989

[54] 4-(BENZISOTHIAZOL-3-YL)PHENOXYA- CETIC ACID 1',1'-DIOXIDES AS DIURETICS

[75] Inventor: Gregory M. Shutske, Somerset, N.J.
[73] Assignee: Hoechst-Roussel Pharmaceuticals, Inc., Somerville, N.J.
[21] Appl. No.: 439,098
[22] Filed: Nov. 3, 1982
[51] Int. Cl.[4] .................. A61K 31/425; C07D 275/06
[52] U.S. Cl. ..................................... 514/373; 548/207
[58] Field of Search .................. 548/207 A; 424/270; 514/373

[56] References Cited

U.S. PATENT DOCUMENTS

| 3,897,476 | 7/1975 | Feit et al. | 424/270 |
| 4,017,632 | 4/1977 | Nachmias et al. | 424/285 |
| 4,337,261 | 6/1982 | Shutske et al. | 548/241 |
| 4,667,041 | 5/1987 | Salzburg | 548/207 |
| 4,728,662 | 3/1988 | Shutske | 514/373 |

FOREIGN PATENT DOCUMENTS

| 845724 | 6/1970 | Canada | 424/272 |
| 2105580 | 9/1972 | Fed. Rep. of Germany | 548/207 |

OTHER PUBLICATIONS

Boshagen et al., "Oxidation products of 3-Amino-1,-2-Benzothiazoles...," *Chem. Ber.* 103:3166–81, (1970).

Beeson et al., *Textbook of Medicine*, vol. II, 14th Ed., W. B. Saunders, Philadelphia, (1975), pp. 990–991.

Primary Examiner—Donald G. Daus
Attorney, Agent, or Firm—Tatsuya Ikeda

[57] ABSTRACT

Novel 4-(benzisothiazol-3-yl)phenoxyacetic acid 1',1'-dioxides of the formula

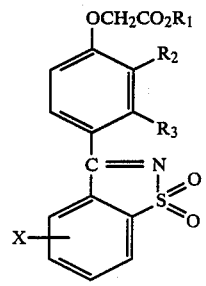

where X is hydrogen, halogen or loweralkyl; $R_1$ is hydrogen or loweralkyl; $R_2$ and $R_3$ are each independently Cl, Br or $CH_3$, and related compounds, methods for preparing same and methods of treatment by administering compositions containing such a compound are described. These compounds are useful as diuretics.

15 Claims, No Drawings

4-(BENZISOTHIAZOL-3-YL)PHENOXYACETIC ACID 1',1'-DIOXIDES AS DIURETICS

This invention relates to novel 4-(benzisothiazol-3-yl)phenoxyacetic acid 1',1'-dioxides, esters thereof and related compounds which are useful in diuretics, to methods of their preparation, to method of treatment with pharmaceutically effective amounts thereof and to pharmaceutical compositions containing such a compound as an active ingredient.

This invention also relates to intermediate compounds useful in the preparation of the above-mentioned compounds and to methods of synthesizing same.

To the best of our knowledge, the compounds of the present invention have not been heretofore made, described or suggested.

One group of the compounds of this invention which are useful as diuretics can be depicted by the general formula

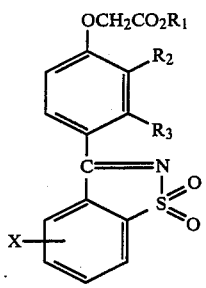

(I)

where X is hydrogen, halogen or loweralkyl; $R_1$ is hydrogen or loweralkyl; $R_2$ and $R_3$ are each independently Cl, Br or $CH_3$. Also included within the scope of the present invention are physiologically acceptable salts of the above-depicted compounds.

Another group of the compounds of this invention which are useful as intermediates for the compounds of formula I can be depicted by the general formula

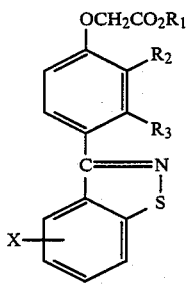

(II)

where X, $R_1$, $R_2$ and $R_3$ are as defined above.

Unless otherwise stated or indicated, the following terms have the following meanings throughout the specification and the appended claims:

"lower" means 1 to 6 carbon atoms;

"loweralkyl" means an alkyl group of 1 to 6 carbon atoms;

"alkyl" means a straight or branched chain hydrocarbon containing no unsaturation;

"halogen" means chlorine, bromine or fluorine.

The physiologically acceptable salts of this invention include those formed with an alkali or alkaline earth metal base or with a non-toxic organic base such as ethanolamine, N-methyl-D-glucamine, etc.

The compounds of the present invention can be prepared according to one or more of the following steps in which X, $R_1$, $R_2$ and $R_3$, unless otherwise indicated, are as defined above.

METHOD A

A phenol or an alkoxybenzene of the formula

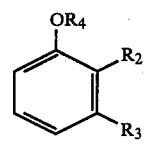

where $R_4$ is hydrogen or loweralkyl, is reacted under Friedel-Crafts conditions with an acid halide of the formula

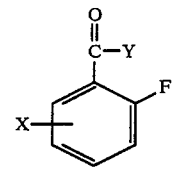

where Y is chlorine or bromine, to provide a compound of the following formula.

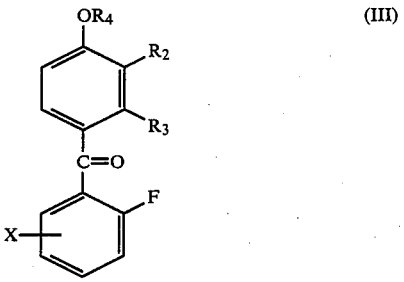

(III)

Preferably, 1,2-dichloroethane is used as a solvent and aluminum chloride as the Friedel-Crafts catalyst.

The compound III is treated with ammonia and elemental sulfur in a suitable solvent such as methoxyethanol at an elevated temperature, e.g. about 150° C., for a sufficient period of time, e.g. 7 hours at 150° C., to provide a benzisothiazole compound of the following formula.

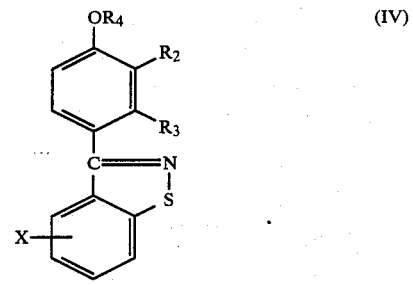

(IV)

The compound IV, when it is an alkoxyphenol compound, namely, when $R_4$ is loweralkyl, is first converted to the corresponding phenol by any conventional deakylation method, e.g. by heating it in a suitable solvent such as 1,2-dichloroethane in the presence of an acid such as boron tribromide.

The phenol compound is reacted with a halogenated acetic acid or an ester thereof of the formula $YCH_2CO_2R_1$, where Y and $R_1$ are as earlier defined, to form the compound II of this invention.

The compound II is oxidized in a conventional manner such as by reaction with a suitable oxidizing agent, e.g., hydrogen peroxide, in a suitable solvent such as acetic acid, to form the compound I of this invention.

All starting materials shown above are either known compounds or are easily prepared by routine methods known to the art from readily available materials.

Effective quantities of the compounds of the invention may be administered to a patient by any of the various methods, for example, orally as in capsules or tablets, parenterally in the form of sterile solutions or suspensions, and in some cases intravenously in the form of sterile solutions. The free acid final products, while effective themselves, may be formulated and administered in the form of their pharmaceutically acceptable addition salts for purposes of stability, convenience of crystallization, increased solubility and the like.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches an the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes, colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of active compound, but may be varied to be between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspension may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple doze vials made of glass or plastic.

The compounds of the invention are useful as diuretics due to their ability to produce diuresis in mammals. Such utility is effected when a compound of the invention is administered to a patient requiring appropriate treatment at an oral, parenteral or intravenous dose of from 1 to 200 mg/kg of body weight per day.

The diuretic activity of the compounds of the subject invention are determined by the diuretic screen test designated as the "Acute Sodium Loaded Mouse" screen. This screen is carried out in the following manner. The acute sodium loaded mouse experiments are performed with groups of male mice weighing 18–24 gms. Drugs are prepared in 1% saline and orally administered in a dosage volume of 10 ml/kg. The animals are housed in metabolic cages, each treatment group consisting of 10 animals, 5 per cage. The tests consist of a vehicle control, a positive control group of 1000 mg/kg urea-treated mice and the potential diuretic agent given at 64 mg/kg.

The resultant pooled urine samples are analyzed for sodium, using a flame photometer. Sodium values are expressed as the mean milliequivalents (mEq)/kg/5 hrs.

Listed below is the diuretic activity of a representative compound of this invention.

| Control | mEq Na$^+$/kg/5 hrs. |
|---|---|
| 4-(Benzisothiazol-3-yl)-2,3-dichlorophenoxyacetic acid 1',1'-dioxide | 2.03 |
| Control | 0.8 |

Compounds of this invention include 4-(benzisothiazol-3-yl)-2,3-dichlorophenoxyacetic acid 1',1'-dioxide and 4-(benzisothiazol-3-yl)-2,3-dichlorophenoxyacetic acid.

The present invention is further illustrated by the following examples of representative compounds and procedures.

EXAMPLE 1

2'-Fluoro-4-methoxy-2,3-dichlorobenzophenone

To a solution of 31.55 g of o-fluorobenzoyl chloride in 100 ml 1,2-dichloroethane, 26.54 g of AlCl$_3$ was added over a 30 minute period. A solution of 32 g of 2,3-dichloroanisole in 50 ml of 1,2-dichloroethane was added dropwise. There was an evolution of gas and the temperature rose to 35°. The mixture was stirred 2 hours and then poured over a mixture of 100 ml concentrated HCl and 100 ml ice. The organic solvent was evaporated in vacuo and the mixture extracted with ether. The ether extract was washed with 10% $K_2CO_3$, washed with water, and dried over $Na_2SO_4$, and the ether was evaporated to give a solid. Recrystallization of the solid from the ether-hexane mixture gave 38.69 g (70%) of 2'-fluoro-4-methoxy-2,3-dichlorobenzophenone, m.p. 74°-77°.

| ANALYSIS | | | |
|---|---|---|---|
| Calculated for $C_{14}H_9Cl_2FO_2$: | 56.21% C | 3.03% H | 6.35% F |
| Found: | 56.20% C | 3.02% H | 6.58% F |

EXAMPLE 2

3-(2,3-Dichloro-4-methoxyphenyl)benzisothiazole

One hundred grams (100 g) of 2'-fluoro-4-methoxy-2,3-dichlorobenzophenone was suspended in 400 ml of methoxy ethanol that was previously saturated with about 50 grams of $NH_3$. Twelve grams (12 g) of elemental sulfur was added to the mixture and the mixture was heated for 7 hours at 150° C. The reaction mixture was cooled and some insoluble material was filtered off. The resulting solution was concentrated under reduced pressure and then purified by high pressure liquid chromatography on silica gel (40% $CH_2Cl_2$/hexane, 250 ml/min) to give 15.80 g (15%) of 3-(2,3-dichloro-4-methoxyphenyl)benzisothiazole. An analytical sample was recrystallized from $CH_3CN$, which had a m.p. 176°-177°.

| ANALYSIS | | | |
|---|---|---|---|
| Calculated for $C_{14}H_9Cl_2NOS$: | 54.20% C | 2.92% H | 4.52% N |
| Found: | 54.25% C | 2.95% H | 4.68% N |

EXAMPLE 3

4-(Benzisothiazol-3-yl)-2,3-dichlorophenoxyacetic acid

A mixture containing 8.2 g of 3-(2,3-dichloro-4-methoxyphenyl)benzisothiazole, 100 ml of 1,2-dichloroethane and 100 ml of $BBr_3$ was refluxed for 30 minutes. It was then poured into ice/water and the organic solvent was removed under reduced pressure. The product was then filtered off, washed with hexane and dried to give 7.50 g (96%) of 4-(benzisothiazol-3-yl)-2,3-dichlorophenol.

The phenol product was warmed at 50° for 30 minutes in 100 ml of dimethylformamide containing 2.90 ml of ethyl bromoacetate and 5.5 g of $K_2CO_3$. Twenty milliliters (20 ml) of 20% aqueous NaOH was then added to the mixture and warming was continued an additional 30 minutes with vigorous stirring. The product acid which was in the sodium salt form was filtered off and washed with water, and then with ether. It was then distributed between 2-butanone and 5% HCl. The organic phase was withdrawn, dried and concentrated under reduced pressure. After recrystallization from acetone/$H_2O$, 8.4 g of a pure product (84% from the methoxy compound), m.p. 224°-226° was obtained.

| ANALYSIS | | | |
|---|---|---|---|
| Calculated for $C_{15}H_9Cl_2NO_2S$: | 50.86% C | 2.56% H | 3.96% N |
| Found: | 50.57% C | 2.64% H | 4.03% N |

EXAMPLE 4

4-(Benzisothiazol-3-yl)-2,3-dichlorophenoxyacetic acid 1',1'-dioxide

A mixture containing 5.0 g of 4-(benzisothiazol-3-yl)-2,3-dichlorophenoxyacetic acid, 200 ml of AcOH and 50 ml of 30% $H_2O_2$ was warmed at 90° for 90 minutes. The reaction mixture was then poured into $H_2O$ and the product filtered off. After recrystallization from EtOAc/hexane, 3.20 g (60%) of an analytically pure product m.p. 230°-232° was obtained.

| ANALYSIS: | | | |
|---|---|---|---|
| Calculated for $C_{15}H_9Cl_2NO_5S$: | 46.64% C | 2.35% H | 3.63% N |
| Found: | 46.67% C | 2.43% H | 3.51% N |

EXAMPLE 5

In a similar manner as Examples 1-3, 2,3-dimethylanisole is converted into 4-(benzisothiazol-3-yl)-2,3-dimethylphenoxyacetic acid.

EXAMPLE 6

The compound obtained in Example 5 is converted into 4-(benzisothiazol-3-yl)-2,3-dimethylphenoxyacetic acid 1',1'-dioxide in a similar manner as Example 4.

I claim:

1. A compound depicted by the formula

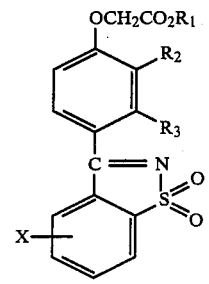

where X is hydrogen, halogen or loweralkyl; $R_1$ is hydrogen or loweralkyl; $R_2$ and $R_3$ are each independently Cl, Br or $CH_3$; and a physiologically acceptable salt thereof.

2. The compound as defined in claim 1 wherein $R_2$ and $R_3$ are chlorine.

3. The compound as defined in claim 1 wherein $R_2$ and $R_3$ are $CH_3$.

4. The compound as defined in claim 1 which is 4-(benzisothiazol-3-yl)-2,3-dichlorophenoxyacetic acid 1',1'-dioxide.

5. The compound as defined in claim 1 which is 4-(benzisothiazol-3-yl)-2,3-dimethylphenoxyacetic acid 1',1'-dioxide.

6. A method of producing diuresis which comprises administering to a patient in need of diuresis a diuretically effective amount of a compound depicted by the formula

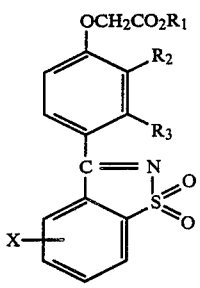

where X is hydrogen, halogen or loweralkyl; $R_1$ is hydrogen or loweralkyl; $R_2$ and $R_3$ are each independently Cl, Br or $CH_3$.

7. The method as defined in claim 6 where said compound has $R_2$ and $R_3$ which are chlorine.

8. The method as defined in claim 6 where said compound has $R_2$ and $R_3$ which are $CH_3$.

9. The method as defined in claim 6 where said compound is 4-(benzisothiazol-3-yl)-2,3-dichlorophenoxyacetic acid 1',1'-dioxide.

10. The method as defined in claim 6 where said compound is 4-(benzisothiazol-3-yl)-2,3-dimethylphenoxyacetic acid 1',1'-dioxide.

11. A pharmaceutical composition comprising a pharmaceutically effective amount of a compound depicted by the formula

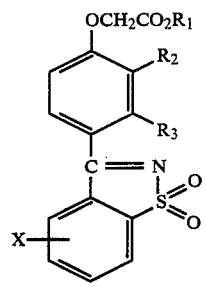

where X is hydrogen, halogen or loweralkyl; $R_1$ is hydrogen or loweralkyl; $R_2$ and $R_3$ are each independently Cl, Br or $CH_3$.

12. The pharmaceutical composition as defined in claim 11 wherein $R_2$ and $R_3$ are chlorine.

13. The pharmaceutical composition as defined in claim 11 wherein $R_2$ and $R_3$ are $CH_3$.

14. The pharmaceutical composition as defined in claim 11 which comprises 4-(benzisothiazol-3-yl)-2,3-dichlorophenoxyacetic acid 1',1'-dioxide.

15. The pharmaceutical composition as defined in claim 11 which comprises 4-(benzisothiazol-3-yl)-2,3-dimethylphenoxyacetic acid 1',1'-dioxide.

* * * * *